United States Patent
Park et al.

(10) Patent No.: US 7,867,880 B2
(45) Date of Patent: Jan. 11, 2011

(54) METAL PRECURSORS FOR LOW TEMPERATURE DEPOSITION AND METHODS OF FORMING A METAL THIN LAYER AND MANUFACTURING A PHASE-CHANGE MEMORY DEVICE USING THE METAL PRECURSORS

(75) Inventors: Hye-young Park, Seongnam-si (KR); Sung-lae Cho, Yongin-si (KR); Byoung-jae Bae, Hwaseong-si (KR); Jin-il Lee, Seongnam-si (KR); Ji-eun Lim, Yongin-si (KR); Young-lim Park, Anyang-si (KR)

(73) Assignee: Samsung Electronics Co., Ltd. (KR)

( * ) Notice: Subject to any disclaimer, the term of this patent is extended or adjusted under 35 U.S.C. 154(b) by 351 days.

(21) Appl. No.: 11/772,494

(22) Filed: Jul. 2, 2007

(65) Prior Publication Data
US 2008/0108174 A1  May 8, 2008

(30) Foreign Application Priority Data
Nov. 7, 2006 (KR) .................. 10-2006-0109580

(51) Int. Cl.
*H01L 21/205* (2006.01)
(52) U.S. Cl. .................. 438/478; 438/102; 438/237; 438/198; 438/381; 257/E21.335; 257/E21.34; 257/E21.459; 257/E21.463

(58) Field of Classification Search .................. 438/102, 438/198, 237, 381, 478, 503, 507; 257/246, 257/247, 248, E21.299, E21.335, E21.34, 257/E21.459, E21.461, E21.463
See application file for complete search history.

(56) References Cited

U.S. PATENT DOCUMENTS

| 6,117,720 A | * | 9/2000 | Harshfield | 438/238 |
| 6,791,102 B2 | * | 9/2004 | Johnson et al. | 257/3 |
| 2007/0053786 A1 | | 3/2007 | Nonaka et al. | |
| 2009/0124039 A1 | * | 5/2009 | Roeder et al. | 438/99 |
| 2009/0305458 A1 | * | 12/2009 | Hunks et al. | 438/102 |

FOREIGN PATENT DOCUMENTS

| JP | 2005-117002 A | 4/2005 |
| KR | 10-2004-0088938 A | 4/2003 |
| KR | 10-2006-0008027 A | 1/2006 |
| KR | 10-2006-0074236 A | 7/2006 |

* cited by examiner

Primary Examiner—Julio J Maldonado
(74) Attorney, Agent, or Firm—Myers Bigel Sibley & Sajovec, PA

(57) ABSTRACT

The present invention provides metal precursors for low temperature deposition. The metal precursors include a metal ring compound including at least one metal as one of a plurality of elements forming a ring. Methods of forming a metal thin layer and manufacturing a phase change memory device including use of the metal precursors is also provided.

14 Claims, 7 Drawing Sheets

METAL PRECURSORS FOR LOW TEMPERATURE DEPOSITION AND METHODS OF FORMING A METAL THIN LAYER AND MANUFACTURING A PHASE-CHANGE MEMORY DEVICE USING THE METAL PRECURSORS

CROSS-REFERENCE TO RELATED PATENT APPLICATION

This application claims priority under 35 U.S.C. §119 to Korean Patent Application No. 10-2006-0109580, filed on Nov. 7, 2006, the disclosure of which is incorporated by reference herein in its entirety.

FIELD OF THE INVENTION

The present invention relates to metal precursors, methods of forming a metal thin layer using the metal precursors, and methods of manufacturing a semiconductor device using the metal precursors.

BACKGROUND OF THE INVENTION

A phase change material is a material that changes into a crystalline state or into an amorphous state in response to changes in temperature. The specific resistance of the phase change material in the crystalline state may be lower than that in the amorphous state. This feature of the phase change material may allow the phase change material to be used in a memory device, for example, a phase-change random access memory (PRAM).

A unit cell of a PRAM includes an access device and a phase change resistor. The phase change resistor generally includes a phase change material layer disposed between a bottom electrode and a top electrode, and the access device is connected to the bottom electrode to transmit a writing current applied to the top electrode.

Figure 1:
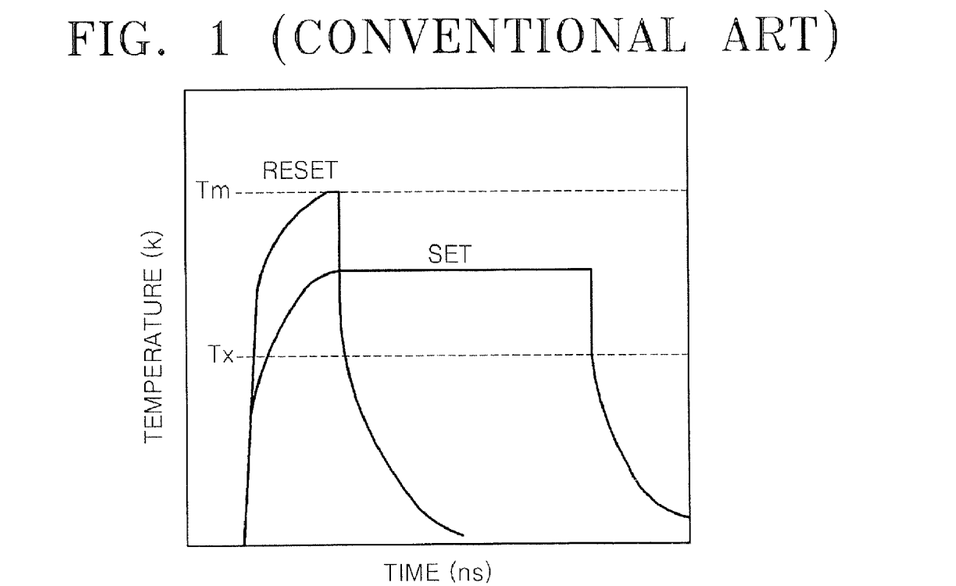
FIG. 1 presents a graph demonstrating a method of performing a set or reset programming operation in a phase change resistor.

FIG. 1 presents a graph that demonstrates a method of performing a set or reset programming operation in a phase change resistor. Specifically referring to FIG. 1, a phase change material layer in an amorphous state is heated to a temperature between a crystallization temperature (Tx) and a melting point (Tm) and then cooled. Thus, the phase change material layer is changed from the amorphous state to a crystalline state (set programming). In contrast, when the phase change material layer is heated to a temperature higher than the melting point (Tm) and the abruptly cooled, the phase change material layer is changed from a crystalline state to an amorphous state (reset programming).

In this instance, the heating temperature applied to the phase change material is adjusted by the amount of a writing current that flows through the bottom electrode and the access device. In other words, when a writing current flows through the bottom electrode and the access device, joule heat is generated at an interface between the bottom electrode and the phase change material layer, and the temperature based upon the joule heat can be determined by the amount of the writing current.

During reset programming, in order to apply a relatively high current, the size of the access device may be enlarged; however, this action can present an obstacle for increasing the device integration. In order to address such a problem, ways of reducing the contact surface area between the bottom electrode and the phase change material layer have been researched in order to increase the effective current density of the writing current. For example, the contact surface area between the bottom electrode and the phase change material layer can be reduced by forming fine via holes exposing fine regions of the bottom electrode and then filling the via holes with a phase change material. However, the phase change material layer is typically formed using a sputtering method, and thus, it may be problematic to fill the via holes without voiding at least due to step coverage of the phase change material layer formed using the sputtering method.

Korean Patent Laid-Open Gazette No. 2006-0008027 discusses a technique of forming a phase change layer in a contact hole using a chemical vapor deposition (CVD) method. In detail, at 700° C., $GeH_4$ is used as the Ge source, one of $Sb(C_2H5)_3$, $Sb(C_3H_7)_3$, $Sb(CH_3)_3$, $Sb(C_2H_3)_3$, and $Sb_4$ is used as the Sb source, and one of $Te(C_2H_5)_3$, $Te(C_2H_3)_3$, $Te(CH_3)_3$, $Te(C_4H_9)_2$, $Te(CH_3)(C_3H_5)$, and $Te(C_3H_5)_2$ is used as the Te source to form a $Ge_2Sb_2Te_5$ phase change material layer. However, it is generally problematic to fill fine contact holes with the phase change material layer at least because of the size of grains of the phase change material layer formed at a relatively high temperature of 700° C.

SUMMARY OF THE INVENTION

The present invention provides metal precursors for low temperature deposition. Embodiments of the present invention provide metal precursors for low temperature deposition including a metal ring compound including at least one metal as one of a plurality of elements forming a ring, wherein the metal precursor is suitable for low temperature deposition.

The present invention also provides methods of forming a metal thin layer using the metal precursors for low temperature deposition. Embodiments of the present invention provide methods of forming a metal thin layer, including supplying to a substrate at least one metal precursor having a metal ring compound, wherein the metal ring compound includes at least one metal as one of a plurality of elements forming a ring, thereby forming a metal thin layer on the substrate.

The present invention also provides methods of manufacturing a phase change memory device, in which fine contact holes can be filled stably, with little to no void formation, using the metal precursor for low temperature deposition. Embodiments of the present invention provide methods of manufacturing a phase change memory device, the methods include: forming a bottom electrode on a substrate; forming a mold insulating layer on the bottom electrode; forming a via hole exposing at least a portion of the bottom electrode in the mold insulating layer; supplying to the substrate to fill the via hole with a phase change material layer a metal precursor including a metal ring compound wherein the metal ring compound including at least one metal as one of a plurality of elements forming a ring; and forming a top electrode on the phase change material layer.

BRIEF DESCRIPTION OF THE DRAWINGS

The above aspects of the present invention will become more apparent by describing in detail various embodiments thereof with reference to the attached drawings in which.

DETAILED DESCRIPTION

The present invention will now be described more fully with reference to the accompanying drawings, in which embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

In the drawings, the size and relative sizes of layers and regions may be exaggerated for clarity. The drawings are not necessarily to scale. Like reference numerals designate like elements throughout the drawings.

It will also be understood that when an element or layer is referred to as being "on," "connected to" and/or "coupled to" another element or layer, the element or layer may be directly on, connected and/or coupled to the other element or layer or intervening elements or layers may be present. In contrast, when an element is referred to as being "directly on," "directly connected to" and/or "directly coupled to" another element or layer, no intervening elements or layers are present.

As used herein, the term "and/or" may include any and all combinations of one or more of the associated listed items and may be abbreviated as "/".

It will also be understood that, although the terms first, second, etc. may be used herein to describe various elements, components, regions, layers and/or sections. These elements, components, regions, layers and/or sections should not be limited by these terms. These terms may be used to distinguish one element, component, region, layer and/or section from another element, component, region, layer and/or section. For example, a first element, component, region, layer and/or section discussed below could be termed a second element, component, region, layer and/or section without departing from the teachings of the present invention.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device may be otherwise oriented (e.g., rotated 90 degrees or at other orientations) and the spatially relative descriptors used herein interpreted accordingly.

The terminology used herein is for the purpose of describing particular embodiments only and is not intended to be limiting of the invention. As used herein, the singular terms "a," "an" and "the" are intended to include the plural forms as well, unless the context clearly indicates otherwise. For example, "a" polymer layer can mean more than one polymer layer unless a single layer is specifically noted.

It will be further understood that the terms "includes" and/or "including," when used in this specification, specify the presence of stated features, integers, steps, operations, elements, and/or components, but do not preclude the presence and/or addition of one or more other features, integers, steps, operations, elements, components, and/or groups thereof.

Unless otherwise defined, all terms (including technical and scientific terms) used herein may have the same meaning as what is commonly understood by one of ordinary skill in the art. It will be further understood that terms, such as those defined in commonly used dictionaries, should be interpreted as having a meaning that is consistent with their meaning in the context of this specification and the relevant art and will not be interpreted in an idealized and/or overly formal sense unless expressly so defined herein. Further, all publications, patent applications, patents, and other references mentioned herein are incorporated by reference in their entirety.

Embodiments of the present invention are described with reference to plan views and cross-sectional illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated as a rectangle will, typically, have rounded or curved features. Thus, the regions illustrated in the figures are schematic in nature of a device and are not intended to limit the scope of the present invention.

Metal Precursors for Low Temperature Deposition

A metal precursor according to some embodiments of the present invention is a metal ring compound including at least one metal as one of a plurality of elements forming the ring. The metal precursor can be applied to a low temperature deposition process. "Low temperature" as it relates to a metal precursor in some embodiments of the present invention is used to indicate that the deposition temperature of the metal precursor is lower than the deposition temperature of a conventional metal precursor. In some embodiments, "low temperature" refers to a temperature of about 300° C. or lower.

The metal precursor according to some embodiments of the present invention can be decomposed at a lower temperature than a conventional metal precursor due at least to a ring strain of the ring compound.

The metal ring compound may be a triangular, tetragonal, pentagonal, hexagonal, heptagonal or octagonal ring compound. The metal ring compound has at least one metal as one of a plurality of elements forming the ring. For example, the triangular metal ring compound has at least one metal at the three vertexes of the ring. In some embodiments, the metal ring compound may be a pentagonal metal ring compound that is relatively stable at a room temperature and has a relatively high ring strain, and thus, has a relatively low decomposition temperature.

The metal forming the metal ring compound may be a metal capable of forming a phase change material. Furthermore, the metal may be germanium (Ge), antimony (Sb) or tellurium (Te).

According to some embodiments of the present invention, the metal ring compound may be a Ge ring compound represented by Formula 1 below:

Formula 1 where the X and Y rings sharing Ge are each independently a triangular, tetragonal, pentagonal, hexagonal, heptagonal or octagonal ring, and another element forming the X ring or the Y ring is independently selected from the group consisting of C, O, N, S, P, Si, Te, Sb, Ge, Se, Sn, Bi, and In, and $R_1$ and $R_2$ are each independently hydrogen, alkyl, allyl, vinyl, amine, halide, cyanide, or an aromatic group.

At least one of the X ring and the Y ring may be pentagonal. Accordingly, an example of the Ge ring compound may be represented by Formula 2 below in which the X ring and the Y ring are pentagonal.

Formula 2 where $R_1$ and $R_2$ are each independently at least one of hydrogen, alkyl, allyl, vinyl, amine, halide, cyanide, or an aromatic group.

Furthermore, $R_1$ and $R_2$ may be hydrogen. Accordingly, another example of the Ge ring compound may be 5-germaspiro[4,4]nonane which is represented by Formula 3 below:

Formula 3

According to another embodiment of the present invention, the metal ring compound may be an Sb ring compound represented by Formula 4 below:

Formula 4 where the X ring including Sb is a triangular, tetragonal, pentagonal, hexagonal, heptagonal or octagonal ring, and another element forming the X ring is selected from the group consisting of C, O, N, S, P, Si, Te, Sb, Ge, Se, Sn, Bi, and In, and $R_1$ and $R_2$ are each independently at least one of hydrogen, alkyl, allyl, vinyl, amine, halide, cyanide, or an aromatic group.

According to another embodiment of the present invention, the metal ring compound may be a Te ring compound represented by Formula 5 below:

Formula 5 where the X ring including Te is a triangular, tetragonal, pentagonal, hexagonal, heptagonal or octagonal ring, and another element forming the X ring is selected from the group consisting of C, O, N, S, P, Si, Te, Sb, Ge, Se, Sn, Bi, and In, and $R_1$ is at least one of hydrogen, alkyl, allyl, vinyl, amine, halide, cyanide, or an aromatic group.

Methods of Forming a Metal Thin Layer Using a Metal Precursor for Low Temperature Deposition A metal thin layer may be formed on a substrate using any of the above-described metal ring compounds. In addition, when a metal thin layer is formed by supplying a plurality of metal precursors to the substrate, at least one of the metal precursors is any one of the above-described metal ring compounds. As described above, the metal ring compound can be decomposed at a low temperature. Thus, a thin layer can be formed at a low temperature unlike in the case where a metal ring compound is not used as a precursor. Further description will be provided later with respect to the examples provided below.

The substrate may be a dielectric layer formed of silicon oxide, titanium oxide, aluminum oxide ($Al_2O_3$), zirconium oxide, or hafnium oxide. The substrate may also be a conductive layer formed of titanium (Ti), titanium nitride (TiN), aluminum, tantalum (Ta), tantalum nitride (TaN), or titanium aluminum nitride (TiAlN). Alternatively, the substrate may be a semiconductor layer formed of silicon or silicon carbide (SiC). Consequently, the metal thin layer according to some embodiments of the present invention may be formed on various types of substrates.

The metal thin layer may be formed using a chemical vapor deposition (CVD) method or an atomic layer deposition (ALD) method. Accordingly, a metal thin layer having, at a minimum, a suitable step coverage can be formed.

According to some embodiments of the present invention, before, generally at the same time as, or after supplying the Ge ring compound represented by one of Formulae 1 through 3 to the substrate, at least one precursor selected from the group consisting of a Si precursor, a Te precursor, an Sb precursor, a Se precursor, a Sn precursor, a Bi precursor, and an In precursor may be further supplied as another precursor. More specifically, when a Te precursor is supplied as another precursor, a Ge—Te layer can be formed on the substrate; and when a Te precursor and a Sb precursor are supplied as other precursors, a Ge—Sb—Te layer can be formed on the substrate.

According to some embodiments of the present invention, generally at the same time as, before or after the Sb ring compound represented by Formula 4 is supplied to the substrate, at least one precursor selected from the group consisting of a Si precursor, a Te precursor, a Ge precursor, a Se precursor, a Sn precursor, a Bi precursor, and an In precursor may be further supplied as another metal precursor. More specifically, when a Te precursor is supplied as another metal precursor, a Sb—Te layer can be formed on the substrate, and when a Te precursor and a Ge precursor are supplied as other metal precursors, a Ge—Sb—Te layer can be formed.

According to some other embodiments of the present invention, generally at the same time as, before or after the Te ring compound represented by Formula 4 is supplied to the substrate, at least one precursor selected from the group consisting of a Si precursor, a Sb precursor, a Ge precursor, a Se precursor, a Sn precursor, a Bi precursor, and an In precursor may be further supplied as another metal precursor. More specifically, when a Ge precursor or a Sb precursor is supplied as another metal precursor, a Ge—Te layer or a Sb—Te layer can be formed on the substrate, and when a Ge precursor and a Sb precursor are supplied as other metal precursors, a Ge—Sb—Te layer can be formed.

In at least some of the embodiments described above, the Ge precursor may be $Ge(CH_3)_4$, $Ge[N(CH_3)_2]_4$, or a Ge ring compound represented by Formula 1. The Sb precursor may be $Sb(CH_3)_3$, $Sb[CH(CH_3)_2]_3$, $Sb[N(CH_3)_2]_3$, or a Sb ring compound represented by Formula 4. The Te precursor may be $Te[CH(CH_3)_2]_2$, $Te[C(CH_3)_3]_2$, or a Te ring compound represented by Formula 5.

Figure 2A:
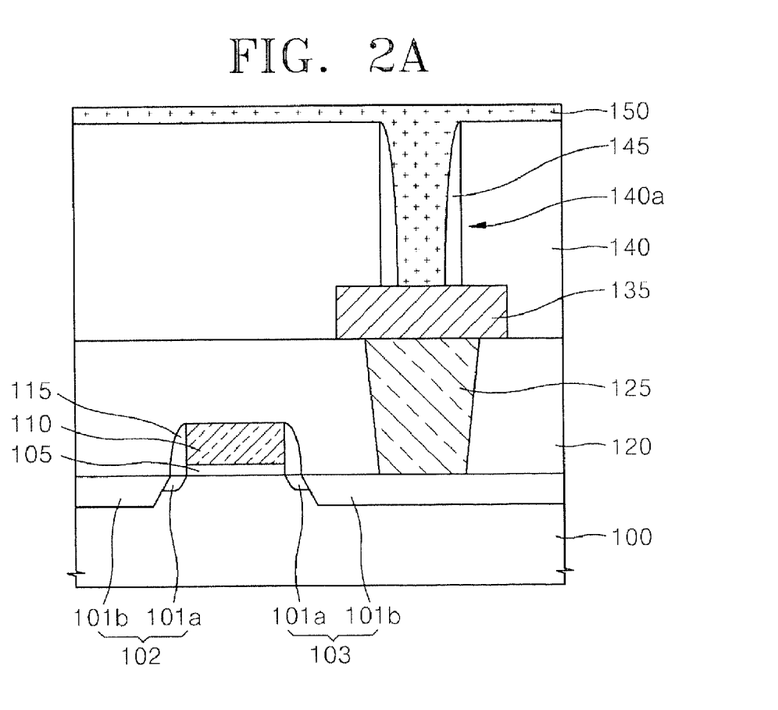
FIGS. 2A and 2B present cross-sectional views illustrating a method of manufacturing a phase change memory device according to some embodiments of the present invention.
Figure 2B:
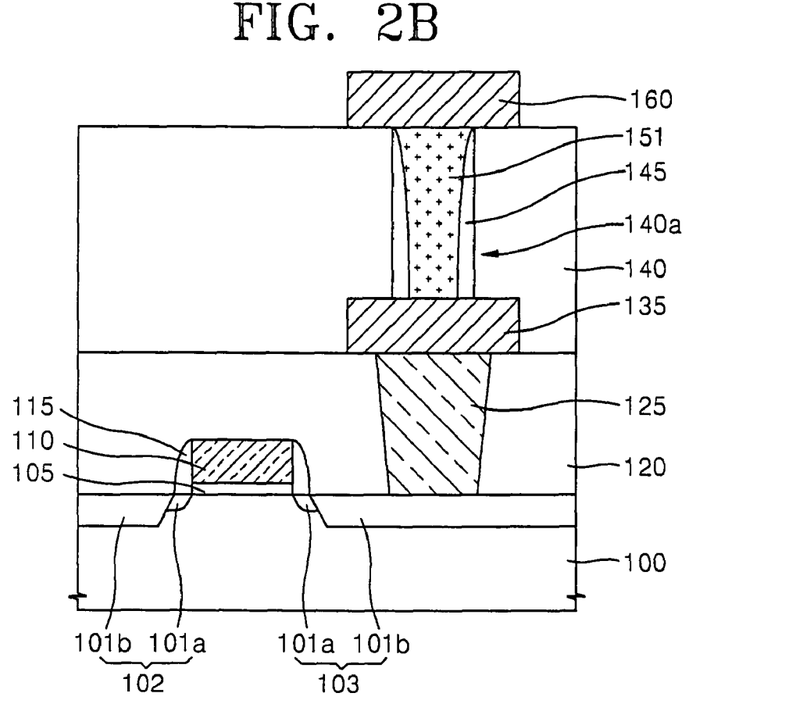

Methods of Manufacturing a Phase Change Memory Device Using a Metal Precursor for Low Temperature Deposition FIGS. 2A and 2B present cross-sectional views illustrating a method of manufacturing a phase change memory device according to some embodiments of the present invention.

Referring to FIG. 2A, a device isolation region (not shown) is formed on a substrate 100 to define an active region. A gate insulating layer 105 and a gate conductive layer are sequentially stacked on the active region, and the gate conductive layer and the gate insulating layer 105 are sequentially etched to form a gate electrode 110. The gate electrode 110 is used as a mask to dope low density impurities into the substrate 100 to form low-density impurity regions 101a that are adjacent to the gate electrode 110 in the substrate 100.

A gate spacer insulating layer is stacked on the substrate 100 in which the low-density impurity regions 101a are formed, and the gate spacer insulating layer is anisotropically etched to form a gate spacer 115 on sidewalls of the gate electrode 110. Subsequently, the gate electrode 110 and the gate spacer 115 are used as a mask to dope high-density impurities into the substrate 100 to form high-density impurity regions 101b that are adjacent to the gate spacer 115.

The low-density impurity regions 101a and the high-density impurity regions 101b form a source/drain region. More specifically, the low-density impurity region 101a and the high-density impurity region 101b on one side of the gate electrode 110 form a source region 102, and the low-density impurity region 101a and the high-density impurity region 101b on the other side of the gate electrode 110 form a drain region 103. The gate electrode 110, the source region 102 and the drain region 103 form a metal oxide semiconductor (MOS) transistor, and the MOS transistor can function as an access device. However, the access device is not limited to a MOS transistor and may also be a diode or bipolar transistor.

A first interlayer insulating layer 120 is formed on the substrate 100 in which the source and drain regions 102 and 103 are formed, and a contact plug 125 contacting the drain region 103 is formed in the first interlayer insulating layer 120. In some embodiments, the contact plug 125 may be formed of a tungsten layer.

A bottom electrode 135 covering the contact plug 125 is formed on the contact plug 125. The bottom electrode 135 may be formed of TiN, TiAlN, TaN, tungsten nitride (WN), molybdenum nitride (MoN), niobium nitride (NbN), a TiSiN layer, titanium boron nitride (TiBN), zirconium silicon nitride (ZrSiN), tungsten silicon nitride (WSiN), tungsten boron nitride (WBN), zirconium aluminum nitride (ZrAlN), molybdenum aluminum nitride (MoAlN), tantalum silicon nitride (TaSiN), tantalum aluminum nitride (TaAlN), titanium tungsten (TiW), titanium aluminum (TiAl), titanium oxynitride (TiON), titanium aluminum oxynitride (TiAlON), tungsten oxynitride (WON), or tantalum oxynitride (TaON).

A mold insulating layer 140 is formed on the first interlayer insulating layer 120 to cover the bottom electrode 135. A via hole 140a exposing a portion of the bottom electrode 135 is formed in the mold insulating layer 140. A hole spacer insulating layer is deposited and anisotropically etched to form a hole spacer 145 on a sidewall of the via hole 140a. Accordingly, the effective diameter of the via hole 140a may be smaller than a resolution limit of a photography process at least due to the hole spacer 145.

Subsequently, a phase change material layer 150 is deposited on the mold insulating layer 140 in which the via hole 140a is formed. The phase change material layer 150 is formed using one of the metal ring compounds described herein as a precursor. More specifically, the substrate 100 having the via hole 140a is loaded into a chamber, and the metal ring compound is supplied into the chamber to form the phase change material layer 150 inside the via hole 140a and on the mold insulating layer 140. Thus, the phase change material layer 150 can be formed at a low temperature that is about 300° C. or lower and at least in part due to the low decomposition temperature of the metal ring compound. The phase change material layer 150 formed at such a low decomposition temperature can have a smaller grain size than a phase change material layer that is formed at a high process temperature. Accordingly, the via hole 140a can be stably filled with phase change material layer 150 with no or limited formation of voids.

According to some embodiments of the present invention, generally at the same time as, after or before a Ge ring compound represented by one of Formulae 1 through 3 is supplied over the substrate 100, a Te precursor may be supplied as another metal precursor. As a result, a Ge—Te layer can be formed as the phase change material layer 150 in the via hole 140a. In other embodiments, generally at the same time as, after or before a Ge ring compound represented by one of Formulae 1 through 3 is supplied over the substrate 100, a Te precursor and a Sb precursor may be supplied as other metal precursors. As a result, a Ge—Sb—Te layer can be formed as the phase change material layer 150 in the via hole 140a. In this instance, the deposition temperature may be 200° C. or greater for stable decomposition of the Ge ring compound. Accordingly, the deposition temperature may be in a range of about 200 to 300° C.

According to some embodiments of the present invention, generally at the same time as, after or before an Sb ring compound represented by Formula 4 is supplied over the substrate 100, a Te precursor may be supplied as another metal precursor. As a result, an Sb—Te layer can be formed as the phase change material layer 150 in the via hole 140a. In other embodiments, generally at the same time as, after or before a Sb ring compound represented by Formula 1 is supplied to the substrate 100, a Te precursor and a Ge precursor may be supplied as other metal precursors. As a result, a Ge—Sb—Te layer can be formed as the phase change material layer 150 in the via hole 140a.

According to some embodiments of the present invention, generally at the same time as, after or before a Te ring compound represented by Formula 5 is supplied over the substrate 100, a Ge precursor or an Sb precursor may be supplied as another metal precursor. As a result, a Ge—Te layer or an Sb—Te layer can be formed as the phase change material layer 150 in the via hole 140a. In other embodiments, generally at the same time as, after or before a Te ring compound represented by Formula 5 is supplied over the substrate 100, a Ge precursor and an Sb precursor may be supplied as other metal precursors. As a result, a Ge—Sb—Te layer can be formed as the phase change material layer 150 in the via hole 140a.

In embodiments described herein, the Ge precursor may be $Ge(CH_3)_4$, $Ge[N(CH_3)_2]_4$, or a Ge ring compound represented by Formula 1. The Sb precursor may be $Sb(CH_3)_3$, $Sb[CH(CH_3)_2]_3$, $Sb[N(CH_3)_2]_3$, or a Sb ring compound represented by Formula 4. The Te precursor may be $Te[CH(CH_3)_2]_2$, $Te[C(CH_3)_3]_2$, or a Te ring compound represented by Formula 5. Accordingly, at least one of the metal precursors is a metal ring compound for forming the phase change material layer 150.

The phase change material layer 150 may be formed using a chemical vapor deposition (CVD) method or an atomic layer deposition (ALD) method.

Figure 3:
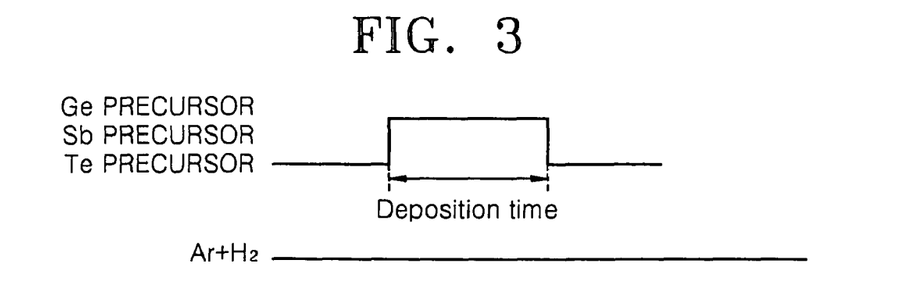
FIG. 3 presents a gas pulsing diagram for forming a Ge—Sb—Te layer using a chemical vapor deposition (CVD) method.

Hereinafter, formation of a Ge—Sb—Te phase change material layer using a CVD method according to some embodiments of the present invention will be described with reference to a gas pulsing diagram illustrated in FIG. 3. Referring to FIGS. 2A and 3, the substrate 100 having the via hole 140a is loaded into a chamber, and an inert gas and a reaction gas are supplied to the chamber and a Ge precursor, an Sb precursor, and a Te precursor are supplied into the chamber at the same time. The inert gas may be Ar, He, or $N_2$, and the reaction gas may be $H_2$, $O_2$, $O_3$, $H_2O$ or $NH_3$. In some embodiments, the inert gas may be Ar, and the reaction gas may be $H_2$. At least one of the Ge precursors, the Sb precursors, and the Te precursors may be a metal ring compound. The Ge precursor, the Sb precursor, or the Te precursor may be each supplied in an amount in a range of 10 to 1000 sccm and for a period of time in a range from 1 to 1000 seconds. The time the Ge precursor, the Sb precursor, and the Te precursor are supplied into the chamber may be defined as a deposition time. The above process may be performed under a pressure in a range from 1 to 10 torr at a temperature in a range from 200 to 300° C. Thus, using the CVD method as described herein, the via hole 140a can be stably filled with the Ge—Sb—Te phase change material layer 150 without voids.

Figure 4:
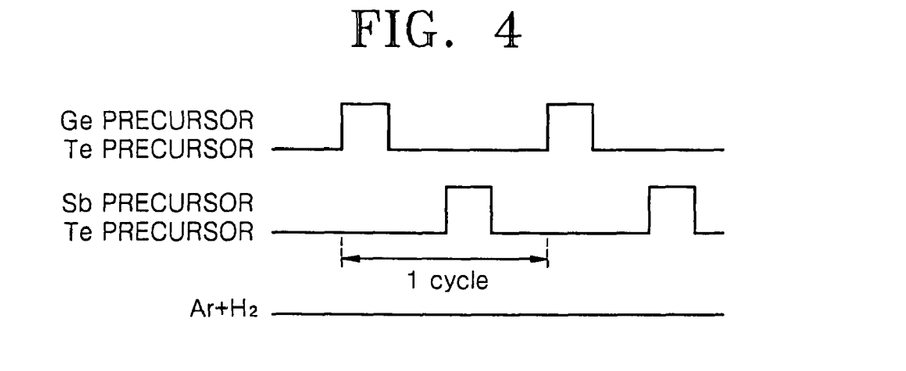
FIG. 4 presents a gas pulsing diagram for forming a Ge—Sb—Te layer using an atomic layer deposition (ALD) method according to some embodiments of the present invention.

Hereinafter, formation of a Ge—Sb—Te phase change material layer using an ALD method according to some embodiments of the present invention will be described with reference to a gas pulsing diagram illustrated in FIG. 4. Referring to FIGS. 2A and 4, the substrate 100 having the via hole 140a is loaded into a chamber, and a Ge precursor, a Sb precursor, and a Te precursor are time-sequentially supplied into the chamber in an amount in a range from about 10 to 1000 sccm and for a period of time in a range from about 0.1 to 60 seconds. At least one of the Ge precursors, the Sb precursors, and the Te precursors may be a metal ring compound. More specifically, 10 to 1000 sccm of the Ge precursor and 10 to 1000 sccm of the Te precursor are supplied for a period of time in a range from about 0.1 to 60 seconds (first step) and then an inert gas and a reaction gas are supplied in an amount in a range from about 10 to 1000 sccm for 0.1 to 60 seconds into the chamber to purge the Ge precursor and the Te precursor physically absorbed on the substrate 100; and unreacted Ge precursor and Te precursor (second step). Subsequently, about 10 to 1000 sccm of the Sb precursor and about 10 to 1000 sccm of the Te precursor are supplied for a period of time in a range from about 0.1 to 60 seconds (third step), and then an inert gas and a reaction gas are supplied in an amount in a range from about 10 to 1000 sccm for a period of time in a range of about 0.1 to 60 seconds to purge the Sb precursor and the Te precursor physically absorbed on the substrate 100; and unreacted Sb precursor and Te precursor (fourth step). The above processes may be performed under a pressure in a range from about 1 to 10 torr at a temperature in a range from about 200 to 300° C. The inert gas may be Ar, He, or $N_2$, and the reaction gas may be $H_2$, $O_2$, $O_3$, $H_2O$ or $NH_3$. In some embodiments, the inert gas may be Ar, and the reaction gas may be $H_2$. The first through fourth steps are regarded as one cycle, and generally 1 to 1000 of such cycles are repeated to stably fill the via hole 140a with a Ge—Sb—Te phase change material layer without voids.

Figure 5:
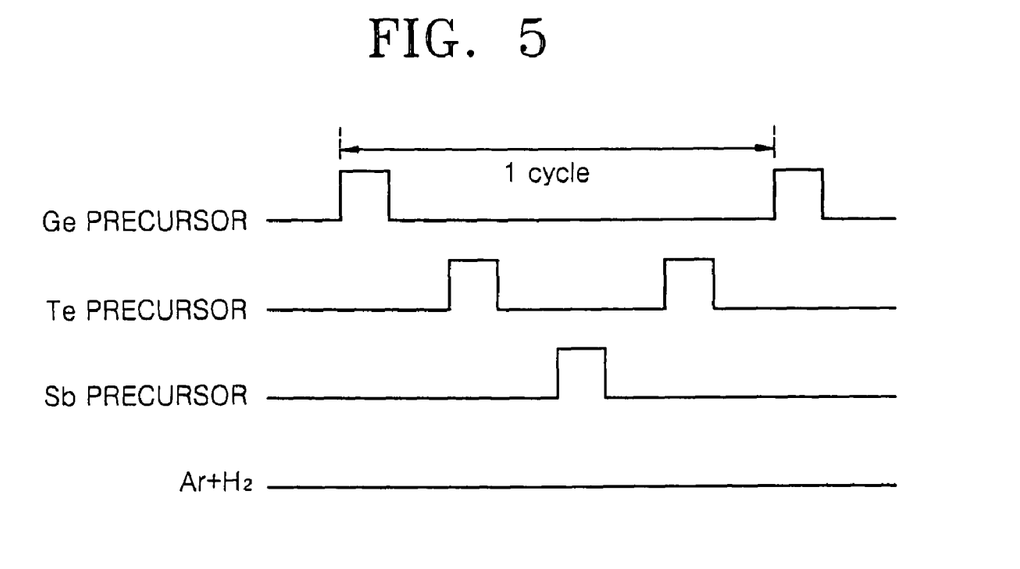
FIG. 5 presents a gas pulsing diagram for forming a Ge—Sb—Te layer using an atomic layer deposition (ALD) method according to some embodiments of the present invention.

Hereinafter, formation of a Ge—Sb—Te phase change material layer using an ALD method according to some embodiments of the present invention will be described with reference to a gas pulsing diagram illustrated in FIG. 5. Referring to FIGS. 2A and 5, the substrate 100 having the via hole 140a is loaded into a chamber, and a Ge precursor, a Sb precursor, and a Te precursor are time-sequentially supplied into the chamber in an amount in a range of about 10 to 1000 sccm and for a period of time in a range of about 0.1 to 60 seconds. At least one of the Ge precursors, the Sb precursors, and the Te precursors may be a metal ring compound. More specifically, about 10 to 1000 sccm of the Ge precursor is supplied for a period of time in a range from about 0.1 to 60 seconds (first step) and then inert gas and reaction gas are supplied in an amount any range of about 10 to 1000 sccm for about 0.1 to 60 seconds into the chamber to purge the Ge precursor physically absorbed on the substrate 100 as well as unreacted Ge precursor (second step). Subsequently, about 10 to 1000 sccm of the Te precursor is supplied for about 0.1 to 60 seconds (third step), and then inert gas and reaction gas are supplied in an amount in a range of about 10 to 1000 sccm for about 0.1 to 60 seconds to purge the Te precursor physically absorbed on the substrate 100 as well as unreacted Te precursor (fourth step). Then about 10 to 1000 sccm of the Sb precursor is supplied for about 0.1 to 60 seconds (fifth step) and then inert gas and a reaction gas are supplied in an amount any range of about 10 to 1000 sccm for about 0.1 to 60 seconds into the chamber to purge the Sb precursor physically absorbed on the substrate 100 as well as unreacted Sb precursor (sixth step). Subsequently, about 10 to 1000 sccm of the Te precursor is supplied for about 0.1 to 60 seconds (seventh step), and then inert gas and a reaction gas are supplied in an amount in a range of about 10 to 1000 sccm for about 0.1 to 60 seconds to purge the Te precursor physically absorbed on the substrate 100 as well as unreacted Te precursor (eighth step). The above processes may be performed under a pressure in a range of about 1 to 10 torr at a temperature in a range of about 200 to 300° C. The inert gas may be Ar, He, or $N_2$, and the reaction gas may be $H_2$, $O_2$, $O_3$, $H_2O$ or $NH_3$. In some embodiments, the inert gas may be Ar, and the reaction gas may be $H_2$. The first through eighth steps are regarded as one cycle, and generally 1 to 1000 of such cycles are repeated to stably fill the via hole 140*a* with a Ge—Sb—Te phase change material layer without or having minimal voids.

Referring to FIG. 2B, after the phase change material layer 150 is planarized to form a planarized phase change material layer 151, a top electrode 160 is formed on the planarized phase changed material layer 151. The phase change material layer 150 can be planarized using an etch-back process or chemical mechanical polishing (CMP) method. As a result, a phase change resistor including the bottom electrode 135, the top electrode 160, and the planarized phase change material layer 151 disposed between the bottom electrode 135 and the top electrode 160 is formed.

Alternatively, a phase change resistor may also be formed by sequentially etching the top electrode 160 and the phase change material layer 150 after a top electrode 160 is formed on the phase change material layer 150.

EXAMPLES

Synthesis Example 1

Synthesis of Ge Ring Compound 24.31 g of metal magnesium (1000 mmol) was suspended in 500 mL of diethyl ether in a reactor of 2 L. After a water bath was installed in the reactor, 130.7 g (500 mmol) of 1,4-dibromobutane was slowly added to the magnesium diethyl ether suspension. Here, the addition speed of 1,4-dibromobutane was adjusted such that the temperature of the reaction solution was maintained at 25° C. After the addition of 1,4-dibromobutane was completed, the reaction solution was agitated for 3 hours at a room temperature. Then 53.6 g (250 mmol) of germanium tetrachloride ($GeCl_4$), which was diluted in 100 mL of diethylether, was slowly added to the reaction solution and then the reaction solution was agitated for 16 hours at a room temperature and then the reaction was completed. After the reaction was completed, the reaction solution was filtered at a reduced pressure to obtain a colorless filtered solution. The colorless filtered solution was fractionally distilled to remove the solvent diethylether and distilled at a reduced pressure (boiling point: 70-71° C. at 10 mmHg) to finally obtain 13.8 g (yield: 30%) of a colorless liquid compound.

Examination Example 1

Figure 6:
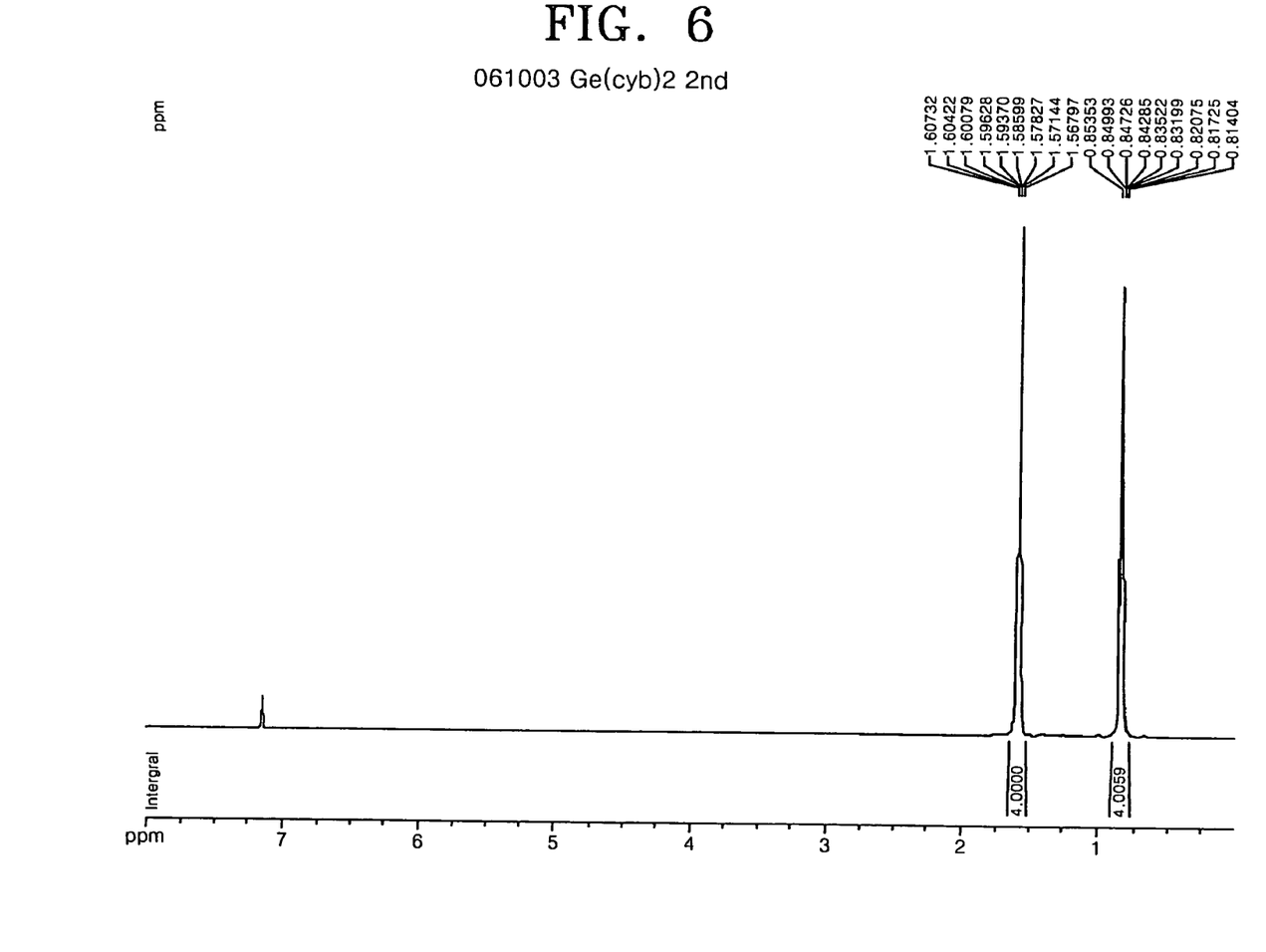
FIG. 6 presents a graph showing $^1$H-NMR analysis of a compound manufactured according to methods described in Synthesis Example 1.

FIG. 6 presents a graph showing $^1$H-NMR analysis of the liquid compound manufactured according to the methods described above in Synthesis Example 1. The $^1$H-NMR analysis was carried out in $C_6D_6$, at 25° C. Referring to FIG. 6, a peak at 1.59 ppm denotes a hydrogen (Ge—$CH_2\underline{CH_2}C$ $\underline{H_2}CH_2$—) that is bonded to a carbon that is not bonded to Ge in Formula 3, and a peak at 0.83 ppm denotes a hydrogen (Ge—$\underline{CH_2}CH_2CH_2\underline{CH_2}$—) that is bonded to carbon that is bonded to Ge in Formula 3. Accordingly, 5-germaspiro[4,4] nonane represented by Formula 3 can be synthesized by the above Synthesis Example 1.

Examination Example 2

Figure 7:
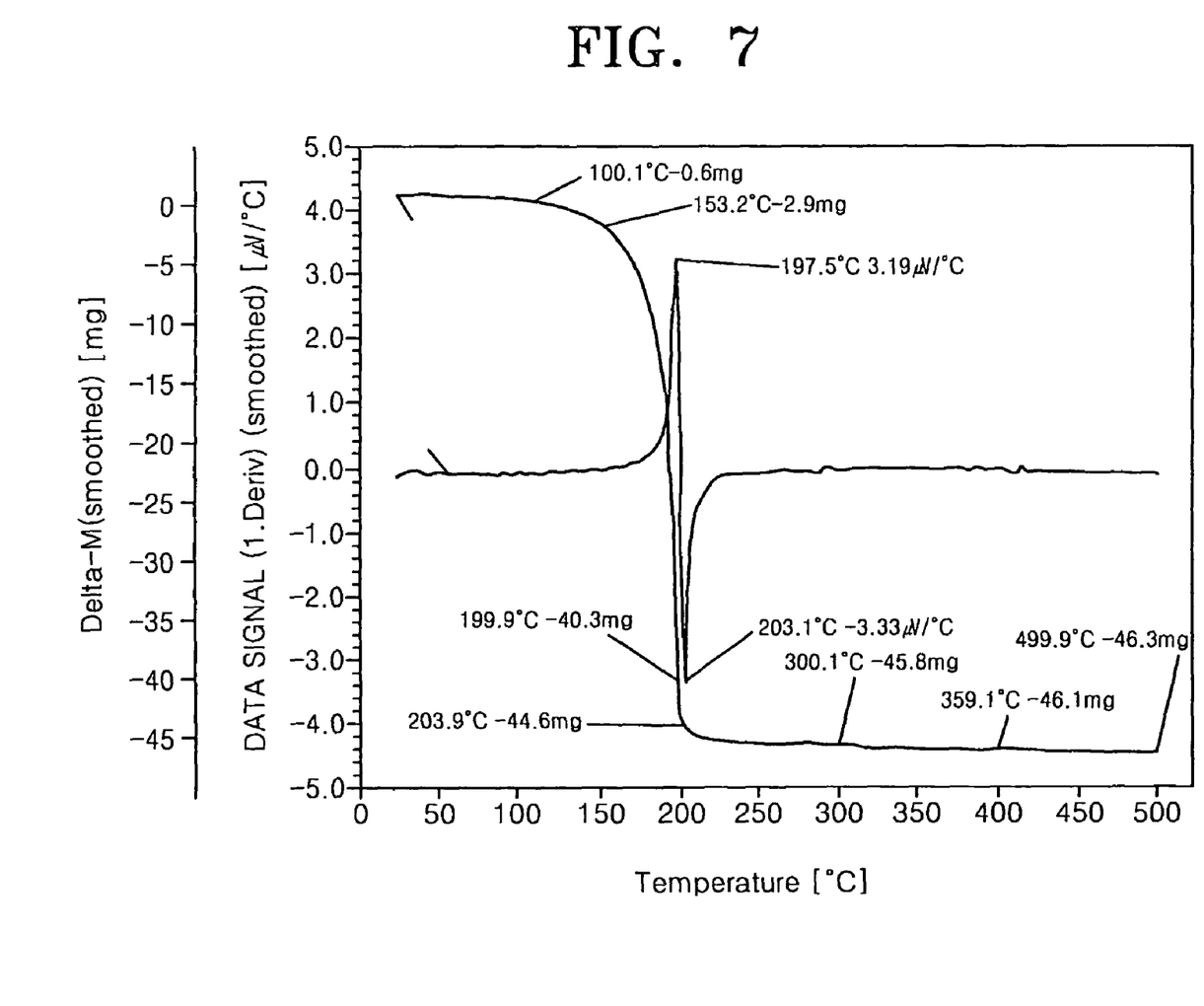
FIG. 7 presents a graph showing differential thermal analysis (DTA) of a compound manufactured according to methods described in Synthesis Example 1.

FIG. 7 presents a graph showing differential thermal analysis (DTA) of the liquid compound, i.e., the Ge ring compound represented by Formula 3, manufactured according to methods described in Synthesis Example 1. Referring to FIG. 7, the Ge ring compound represented by Formula 3 is thermally decomposed at about 200° C., and thus, generates Ge.

Manufacturing Example 1

Examination of Formation of Layers at a Low Temperature Deposition

A titanium oxide substrate was loaded into a chamber. 100 sccm of a Ge precursor, i.e., a Ge ring compound, represented by Formula 3; and 100 sccm of a Te precursor, i.e., Te(C $(CH_3)_3)_2$, were supplied for 2 seconds into the chamber (first step). 500 sccm of Ar and 500 sccm of $H_2$ were supplied into the chamber for 5 seconds to purge the Ge precursor and Te precursor physically absorbed on the substrate; and unreacted Ge precursor and Te precursor (second step). Then, 100 sccm of a Sb precursor, i.e., $Sb(CH(CH_3)_2)_3$; and 100 sccm of a Te precursor, i.e., $Te(C(CH_3)_3)_2$, were supplied for 2 seconds into the chamber (third step). 500 sccm of Ar and 500 sccm of $H_2$ were supplied into the chamber for 5 seconds to purge the Sb precursor and Te precursor physically absorbed on the substrate; and unreacted Sb precursor and Te precursor (fourth step). Here, the above first through fourth steps are regarded as one cycle and 100 such cycles were repeated to form a Ge—Sb—Te layer. The temperature of the substrate was maintained at 260° C., and the pressure inside the chamber was 5 torr.

Comparative Example 1

A Ge—Sb—Te layer was formed in the same manner as in the methods described in Manufacturing Example 1 except that the temperature of the substrate was maintained at 350° C. and $Ge(CH_2CHCH_2)_4$ was used as a Ge precursor.

Figure 8:
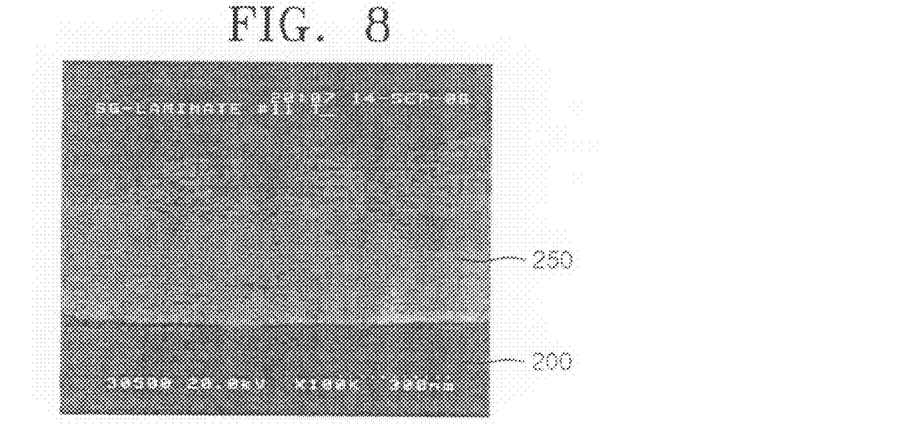
FIG. 8 presents a photographic image of a Ge—Sb—Te layer formed according to methods described in Manufacturing Example 1.
Figure 9:
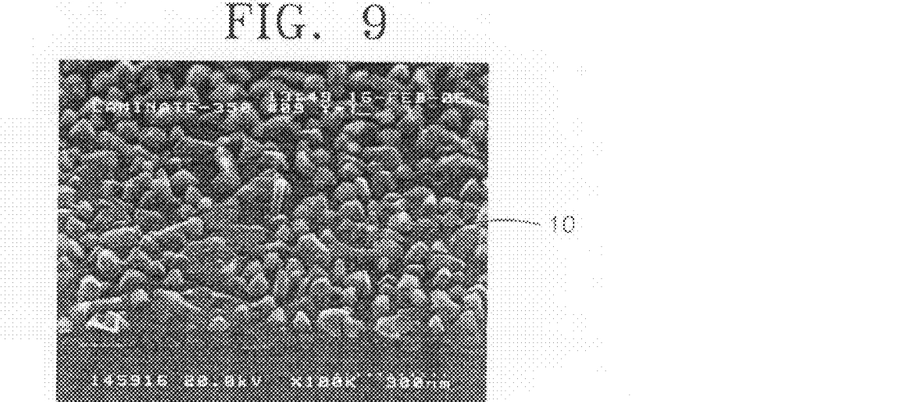
FIG. 9 presents a photographic image of a Ge—Sb—Te layer formed according to methods described in Comparative Example 1.

FIGS. 8 and 9 are photographic images respectively showing Ge—Sb—Te layers formed according to methods described in Manufacturing Example 1 and Comparative Example 1. Referring to FIG. 8, a Ge—Sb—Te layer 250 is formed on the substrate 200. In some embodiments of the present invention, a phase change material layer can be formed at a temperature that is lower than 300° C. or lower, such as about 260° C., using a Ge ring compound. Furthermore, the Ge—Sb—Te layer 250 has a relatively small grain size.

Referring to FIG. 9, a Ge—Sb—Te layer 10 is formed on the substrate. However, the Ge—Sb—Te layer 10 is formed at a high temperature of 350° C. Furthermore, the Ge—Sb—Te layer 10 has a relatively greater grain size compared to the Ge—Sb—Te layer 250 illustrated in FIG. 7.

Manufacturing Example 2

Examination of Ge—Sb—Te Layer in a Fine Via Hole

A substrate including a via hole having an effective diameter of 50 nm was loaded into a chamber. More specifically, 100 sccm of a Ge precursor, i.e., a Ge ring compound represented by Formula 3; and 100 sccm of a Te precursor, i.e., $Te(C(CH_3)_3)_2$, were supplied for 2 seconds into the chamber (first step). Then 500 sccm of Ar and 500 sccm of $H_2$ were supplied for 5 seconds into the chamber to purge the Ge precursor and the Te precursor physically absorbed on the substrate; and unreacted Ge precursor and Te precursor (second step). Next, 100 sccm of an Sb precursor, such as $Sb(CH(CH_3)_2)_3$, and 100 sccm of a Te precursor, such as $Te(C(CH_3)_3)_2$, were supplied for 2 seconds into the chamber (third step). 500 sccm of Ar and 500 sccm of $H_2$ were supplied for 5 seconds into the chamber to purge the Sb precursor and the Te precursor physically absorbed on the substrate; and unreacted Sb precursor and Te precursor (fourth step). Here, the first through fourth steps are regarded as one cycle, and 100 such cycles were repeated to form a Ge—Sb—Te layer in the via hole. The temperature of the substrate was maintained at 280° C., and the pressure in the chamber was 5 torr.

Figure 10:
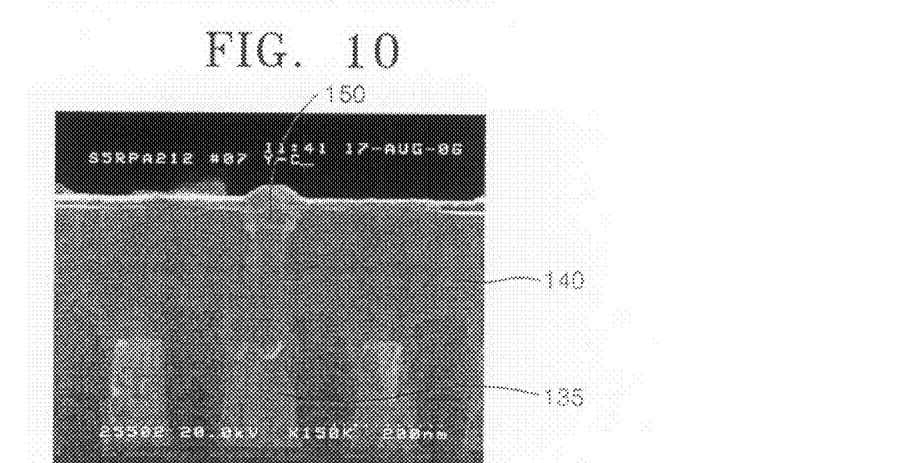
FIG. 10 presents a scanning electron microscope (SEM) image showing a cross-section of a phase change memory device manufactured according to methods described in Manufacturing Example 2.

FIG. 10 presents a scanning electron microscope (SEM) image showing a cross-section of a phase change memory device manufacturing according to methods of Manufacturing Example 2.

As can be seen in FIG. 10, a Ge—Sb—Te layer, that is, a phase change material layer 150 is stably filled in the via hole having an effective diameter of about 50 nm without the formation of voids.

Manufacturing Example 3

Examination of a Ge—Sb—Te Layer Manufactured Using a CVD Method

A titanium oxide layer substrate was loaded into a chamber. 100 sccm of a Ge precursor, i.e., Ge ring compound represented by Formula 3; 100 sccm of an Sb precursor, that is, $Sb(CH(CH_3)_2)_3$; and 100 sccm of a Te precursor, that is, $Te(C(CH_3)_3)_2$, were supplied for 100 seconds into the chamber. Simultaneously, 500 sccm of Ar was supplied into the chamber to form a Ge—Sb—Te layer. The temperature of the substrate was maintained at about 260° C., and the pressure in the chamber was about 5 torr.

Manufacturing Example 4

A Ge—Sb—Te layer was formed in the same manner as described in the methods in Manufacturing Example 3 except that 100 sccm of $H_2$ was supplied at the same time with 500 sccm of Ar into the chamber.

Manufacturing Example 5

A Ge—Sb—Te layer was formed in the same manner as described in the methods in Manufacturing Example 3 except that 500 sccm of $H_2$ was supplied at the same time with 500 sccm of Ar into the chamber.

Manufacturing Example 6

A Ge—Sb—Te layer was formed in the same manner as described in the methods in Manufacturing Example 3 except that 1000 sccm of $H_2$ was supplied at the same time with 500 sccm of Ar into the chamber.

Figure 11:
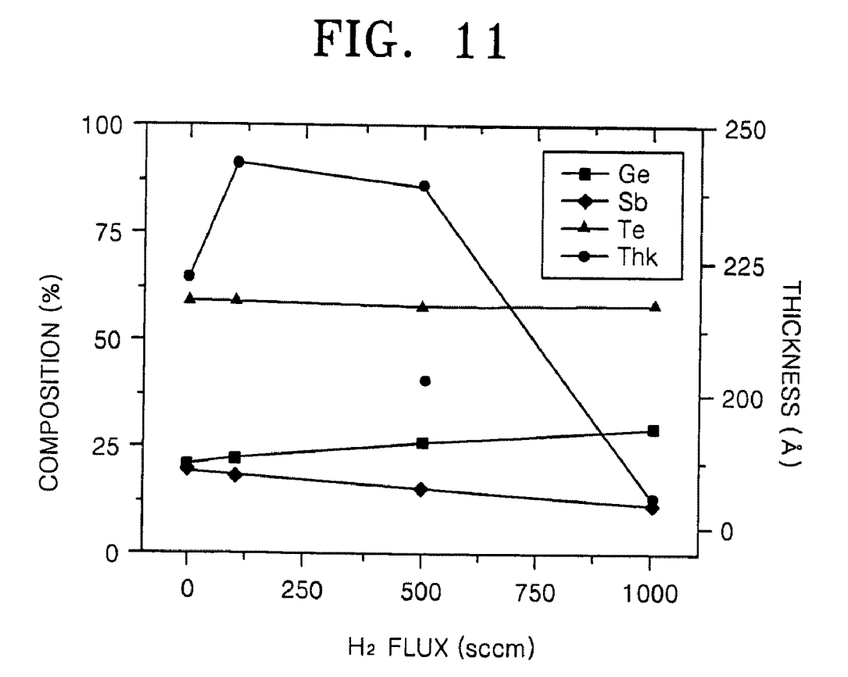
FIG. 11 presents a graph showing the composition and thickness of the Ge—Sb—Te layer manufactured according to methods described in Manufacturing Examples 3 through 6.

FIG. 11 presents a graph showing the composition and thickness of the Ge—Sb—Te layer manufactured according to methods described in Manufacturing Examples 3 through 6. Referring to FIG. 11, the composition ratio of the Ge—Sb—Te layer can vary according to the $H_2$ flux quantity. Accordingly, the composition ratio of the Ge—Sb—Te layer can be adjusted by adjusting the $H_2$ flux quantity. Also, the deposition temperature of a conventional Ge—Sb—Te layer is relatively high, and thus, it may be problematic to adjust the composition ratio of the Ge—Sb—Te layer; however, since the deposition temperature of the Ge—Sb—Te layer according to embodiments of the present invention is 300° C. or lower, the composition ratio of the Ge—Sb—Te layer can be adjusted.

Manufacturing Example 7

Examination of a Ge—Sb—Te Layer Manufactured Using an ALD Method

A titanium oxide layer substrate was loaded into a chamber. More specifically, 100 sccm of a Ge precursor, i.e., a Ge ring compound represented by Formula 3; and 100 sccm of a Te precursor, i.e., $Te(C(CH_3)_3)_2$, were supplied for 2 seconds into the chamber (first step). Then 500 sccm of Ar and 500 sccm of $H_2$ were supplied for 5 seconds into the chamber to purge the Ge precursor and the Te precursor physically absorbed on the substrate; and unreacted Ge precursor and Te precursor (second step). Next, 100 sccm of an Sb precursor, i.e., $Sb(CH(CH_3)_2)_3$, and 100 sccm of a Te precursor, i.e., $Te(C(CH_3)_3)_2$, were supplied for 1 second into the chamber (third step). The ratio of the supplying time of Sb—Te precursors to the supplying time of the Ge—Te precursors is set to be 0.5. 500 sccm of Ar and 500 sccm of $H_2$ were supplied into the chamber to purge the Sb precursor and Te precursor physically absorbed on the substrate; and unreacted Sb precursor and Te precursor (fourth step). Here, the first through fourth steps are regarded as one cycle; and 100 such cycles were repeated to form a Ge—Sb—Te layer. The temperature of the substrate was maintained at 260° C.

Manufacturing Example 8

A Ge—Sb—Te layer was formed in the same manner as described in the methods in Manufacturing Example 7 except that 100 sccm of a Sb precursor, that is, $Sb(CH(CH_3)_2)_3$, and 100 sccm of a Te precursor, i.e., $Te(C(CH_3)_3)_2$ were supplied into the chamber in the third step for 2 seconds in order for the ratio of the supplying time of Sb—Te precursors to the supplying time of Ge—Te precursors to be 1, i.e., 2 seconds/2 seconds.

Manufacturing Example 9

A Ge—Sb—Te layer was formed in the same manner as described in the methods in Manufacturing Example 7 except that 100 sccm of a Sb precursor, that is, $Sb(CH(CH_3)_2)_3$, and 100 sccm of a Te precursor, i.e., $Te(C(CH_3)_3)_2$ were supplied into the chamber in the third step for 3 seconds in order for the ratio of the supplying time of Sb—Te precursors to the supplying time of Ge—Te precursors to be 1.5., i.e., 3 seconds/2 seconds).

Figure 12:
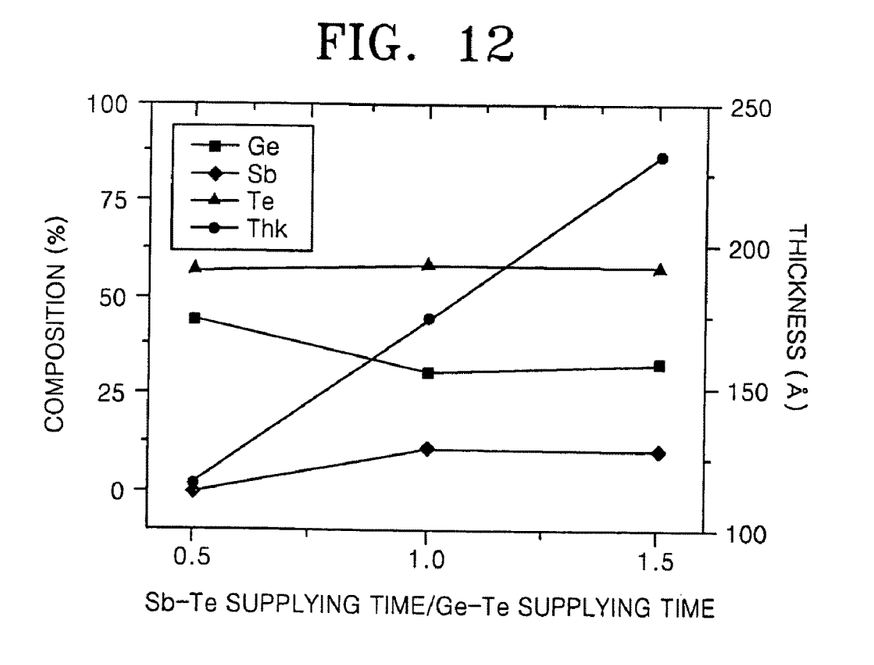
FIG. 12 presents a graph showing the composition and thickness of the Ge—Sb—Te layer manufactured according to methods described in Manufacturing Examples 7 through 9.

FIG. 12 presents a graph showing the composition and thickness of the Ge—Sb—Te layer manufactured according to methods described in Manufacturing Examples 7 through 9. Referring to FIG. 12, the composition of the Ge—Sb—Te layer varies according to the ratio of the supplying time of Sb—Te precursors to the supplying time of Ge—Te precursors. Accordingly, the composition of the Ge—Sb—Te layer can be adjusted by adjusting the ratio of the supplying time of the Sb—Te precursors with respect to the supplying time of the Ge—Te precursors. Also, conventionally, the deposition temperature of the Ge—Sb—Te layer was relatively high, and thus, it was generally problematic to adjust the composition ratio of the Ge—Sb—Te layer; however, since the deposition temperature of the Ge—Sb—Te layer according to some embodiments of the present invention is 300° C. or lower, the composition ratio of the Ge—Sb—Te layer can be adjusted.

As described above, according to some embodiments of the present invention, the deposition temperature of a metal thin layer (or a phase change material layer) can be reduced by using a metal ring compound as a metal precursor. Therefore, the metal thin layer (or the phase change material layer) formed using the metal ring compound as a metal precursor can have a smaller grain size thereby filling fine via holes with minimal to no formation of voids.

While the present invention has been particularly shown and described with reference to embodiments thereof, it will be understood by those of ordinary skill in the art that various changes in form and details may be made therein without departing from the spirit and scope of the present invention as defined by the following claims.

What is claimed is:

1. A method of forming a metal thin layer, comprising supplying to a substrate at least one metal precursor having a metal ring compound, wherein said metal ring compound comprises at least one metal as one of a plurality of elements forming a ring, thereby forming a metal thin layer on the substrate,
wherein the metal ring compound is a Ge ring compound represented by Formula 1:

Formula 1 wherein
X and Y rings comprising Ge are each independently a triangular, tetragonal, a pentagonal, hexagonal, heptagonal or octagonal ring, and each of the X and Y rings consists of C and H; and
$R_1$ and $R_2$ are each independently at least one of hydrogen, an alkyl group, an allyl group, a vinyl group, an amine group, a halide, a cyanide, or an aromatic group.

2. The method of claim 1, wherein the metal forms a phase change material.

3. The method of claim 1, wherein the metal thin layer is formed at a temperature in a range of about 200 to 300° C.

4. The method of claim 3, wherein the temperature is about 300° C. or lower.

5. The method of claim 1, wherein a further precursor comprising Si, Te, Sb, Se, Sn, Bi or In is supplied to the substrate together with the at least one metal precursor.

6. The method of claim 1, wherein the substrate comprises silicon oxide, titanium oxide, aluminum oxide ($Al_2O_3$), zirconium oxide, or hafnium oxide.

7. The method of claim 1, wherein the substrate comprises titanium (Ti), titanium nitride (TiN), silicon, aluminum, silicon carbide (SiC), tantalum (Ta), tantalum nitride (TaN), or titanium aluminum nitride (TiAlN).

8. The method of claim 1, wherein the metal thin layer is formed using a chemical vapor deposition (CVD) method or an atomic layer deposition (ALD) method.

9. A method of manufacturing a phase change memory device, the method comprising:
forming a bottom electrode on a substrate;
forming a mold insulating layer on the bottom electrode;
forming a via hole exposing at least a portion of the bottom electrode in the mold insulating layer;
supplying to the substrate to fill the via hole with a phase change material layer a metal precursor comprising a metal ring compound wherein the metal ring compound comprises at least one metal as one of a plurality of elements forming a ring; and
forming a top electrode on the phase change material layer,
wherein the metal ring compound is a Ge ring compound represented by Formula 1:

Formula 1 wherein
X and Y rings comprising Ge are each independently a triangular, tetragonal, a pentagonal, hexagonal, heptagonal or octagonal ring, and each of the X and Y rings consists of C and H; and
$R_1$ and $R_2$ are each independently at least one of hydrogen, an alkyl group, an allyl group, a vinyl group, an amine group, a halide, a cyanide, or an aromatic group.

10. The method of claim 9, wherein a Te precursor is further supplied to the substrate to form a Ge—Te layer as the phase change material layer.

11. The method of claim 9, wherein a Sb precursor and a Te precursor are further supplied to the substrate to form a Ge—Sb—Te layer as the phase change material layer.

12. The method of claim 9, wherein the bottom electrode comprises Ti, TiN, TiAlN, TaN, tungsten nitride (WN), molybdenum nitride (MoN), niobium nitride (NbN), TiSiN, titanium boron nitride (TiBN), zirconium silicon nitride (ZrSiN), tungsten silicon nitride (WSiN), tungsten boron nitride (WBN), zirconium aluminum nitride (ZrAlN), molybdenum aluminum nitride (MoAlN), tantalum silicon nitride (TaSiN), tantalum aluminum nitride (TaAlN), titanium tungsten (TiW), titanium aluminum (TiAl), titanium oxynitride (TiON), titanium aluminum oxynitride (TiAlON), tungsten oxynitride (WON), or tantalum oxynitride (TaON).

13. The method of claim 9, wherein the phase change material layer is formed using a chemical vapor deposition (CVD) method or an atomic layer deposition (ALD) method.

14. The method of claim 9, wherein, before the phase change material layer is formed, an insulating spacer is further formed on sidewalls of the via hole.

* * * * *